United States Patent [19]

Robinson et al.

[11] Patent Number: 5,519,197
[45] Date of Patent: May 21, 1996

[54] MEDICAL SURGICAL DEVICE WITH COUNTER FOR RECORDING USAGE

[75] Inventors: Janine C. Robinson, Half Moon Bay; Isidro M. Gandionco, Fremont; Jeffrey J. Christian, San Jose; Elisha A. Tal, San Francisco, all of Calif.

[73] Assignee: Unisurge, Inc., Cupertino, Calif.

[21] Appl. No.: 393,139

[22] Filed: Feb. 21, 1995

Related U.S. Application Data

[63] Continuation of Ser. No. 80,754, Jun. 22, 1993, Pat. No. 5,448,042.

[51] Int. Cl.[6] .................... G06M 1/00; G09F 9/00
[52] U.S. Cl. .................... 235/103; 235/118; 116/306
[58] Field of Search .................... 235/103, 118, 235/123; 116/306, 309, 311, 312, 315, 284

[56] References Cited

U.S. PATENT DOCUMENTS

| | | | |
|---|---|---|---|
| 4,011,829 | 3/1977 | Waschsmann et al. | 116/121 |
| 4,365,722 | 12/1982 | Kramer | 215/220 |
| 4,749,093 | 6/1988 | Trick | 116/308 |
| 4,782,966 | 11/1988 | Thackrey | 116/308 |
| 5,261,548 | 11/1993 | Barker et al. | 215/230 |
| 5,280,834 | 1/1994 | Berkley | 116/309 |

*Primary Examiner*—Michael L. Gellner
*Assistant Examiner*—Eddie C. Lee
*Attorney, Agent, or Firm*—Flehr, Hohbach, Test, Albritton & Herbert

[57] ABSTRACT

Medical device having a counter for recording usage. A medical tool is provided having a proximal extremity. The tool having a collar fixed thereto and a cap. The cap includes a part which requires replacement and/or cleaning for each use of the tool. A detent assembly is carried by the cap and the collar and includes a rotatable counter wheel and a mechanism for causing advancement of the counter wheel from one number to the next number when the cap is separated from the collar so that the counter wheel is advanced by one increment each time the cap is removed and/or replaced on the collar to give an indication of the number of times that the device has been used.

6 Claims, 3 Drawing Sheets

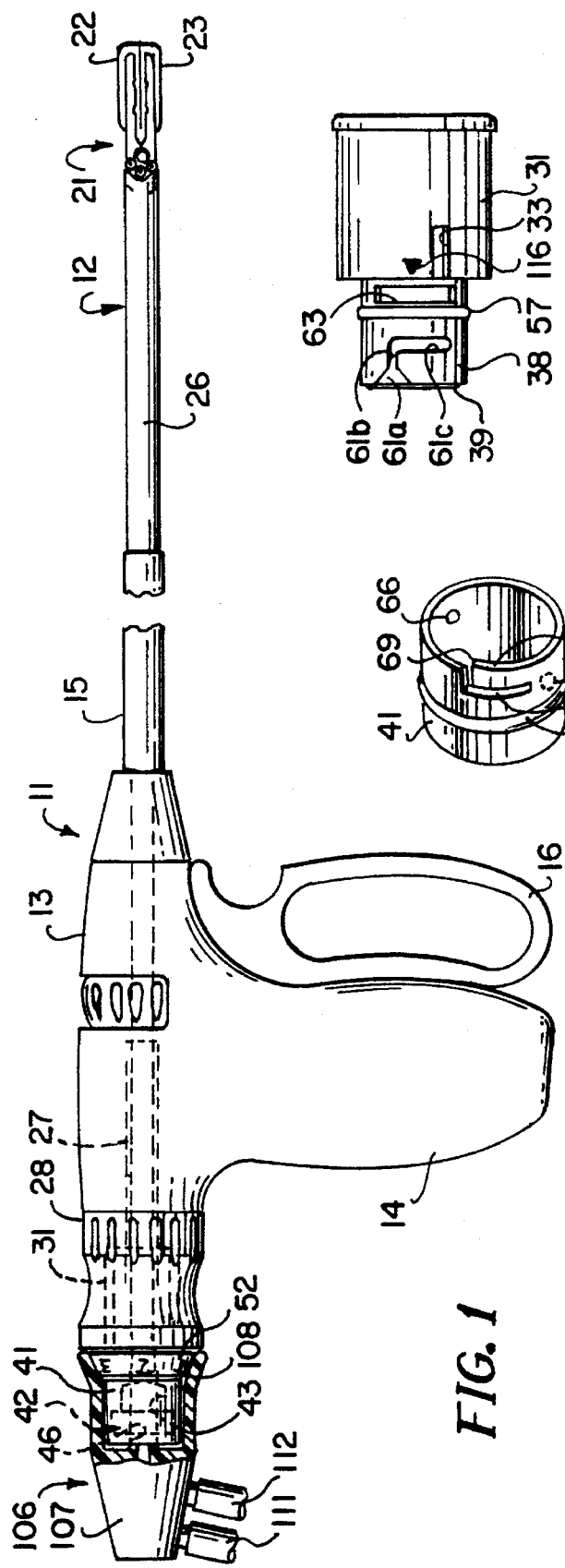
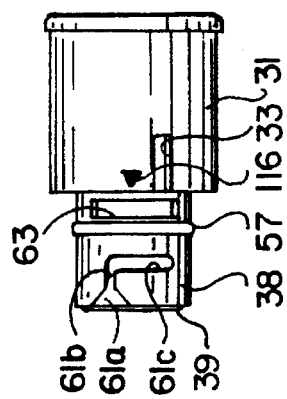
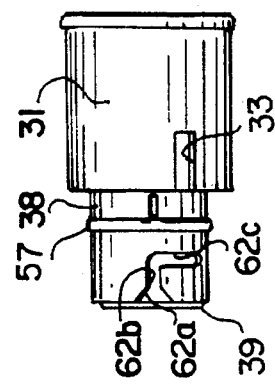
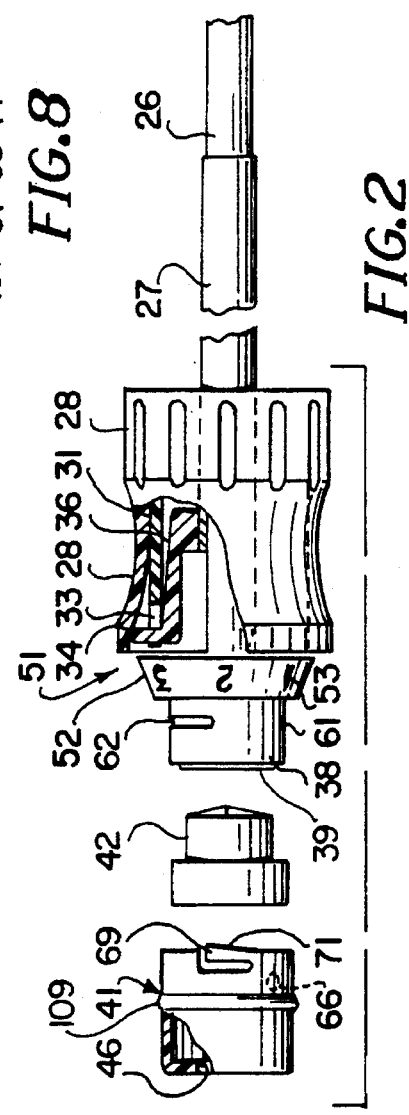

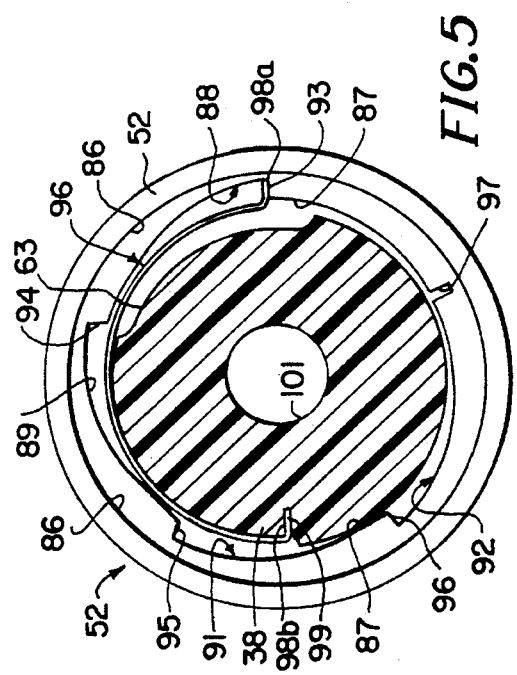
FIG. 5
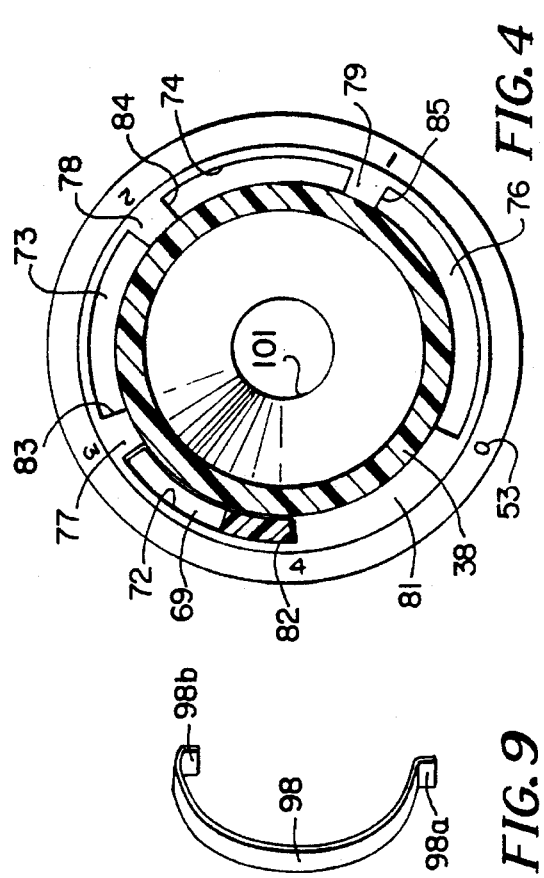
FIG. 4
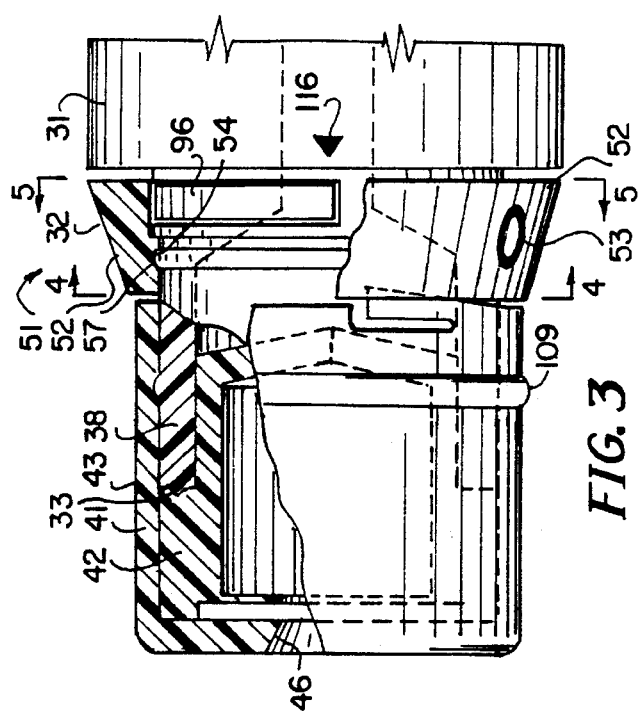
FIG. 3
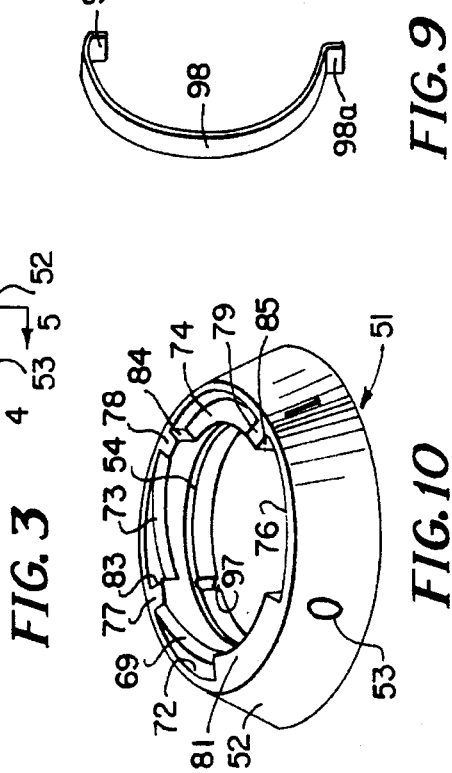
FIG. 9
FIG. 10

MEDICAL SURGICAL DEVICE WITH COUNTER FOR RECORDING USAGE

This is a continuation of application Ser. No. 08/080,754 filed Jun. 22, 1993, now U.S. Pat. No. 5,448,042.

This invention relates to a surgical device with a counter for recording usage.

Various types of medical devices have heretofore been provided, as for example tools which are utilized in laparoscopic surgery. With such medical devices a need has arisen for ascertaining the number of times a tool has been used, particularly where the tool is of a reusable type but has a limited lifetime. Such usage counting is particularly desirable for warranty purposes.

In general, it is an object of the present invention to provide a medical device, which is provided, with a counter for recording usage.

Another object of the invention is to provide a medical device of the above character which requires sterilization and/or cleaning before each use.

Another object of the invention is to provide a medical device of the above character which utilizes a removable part which must be removed for cleaning and/or sterilization purposes and must be replaced for reuse of the medical device.

Another object of the invention is to provide a medical device of the above character in which the counter is advanced by one increment each time the removable part is removed.

Another object of the invention is to provide a medical device of the above character in which the removable part includes a cap.

Another object of the invention is to provide a medical device of the above character in which the counter is very compact and is disposed within the normal outlines of the medical device.

Additional objects and features of the invention will appear from the following description in which the preferred embodiments are set forth in detail in conjunction with the accompanying drawing.

FIG. 1 is a side elevational view of a tool actuator which has an mounted therein a medical device or tool which is provided with a counter for recording usage with certain portions being shown in cross section.

FIG. 2 is a partially exploded view partially in cross section of the medical device shown in FIG. 1.

FIG. 3 is an enlarged view partially in cross section of the proximal extremity of the medical device as shown in FIG. 1.

FIG. 4 is a cross sectional view taken along the line 4—4 of FIG. 3.

FIG. 5 is a cross sectional view taken along the line 5—5 of FIG. 3.

FIG. 6 is a side elevation of a view of a collar or skirt with its cylindrical extension utilized in the medical device shown in FIG. 1.

FIG. 7 is a view similar to FIG. 6 but rotated by 180°.

FIG. 8 is a isometric view of the cap utilized in the medical device shown in FIGS. 1 and 2.

FIG. 9 is a isometric view of the spring utilized in the counter assembly of the medical device shown in FIGS. 1 and 2.

FIG. 10 is an isometric view of the counter ring forming a part of the medical device shown in FIGS. 1 and 2.

Figure 13:
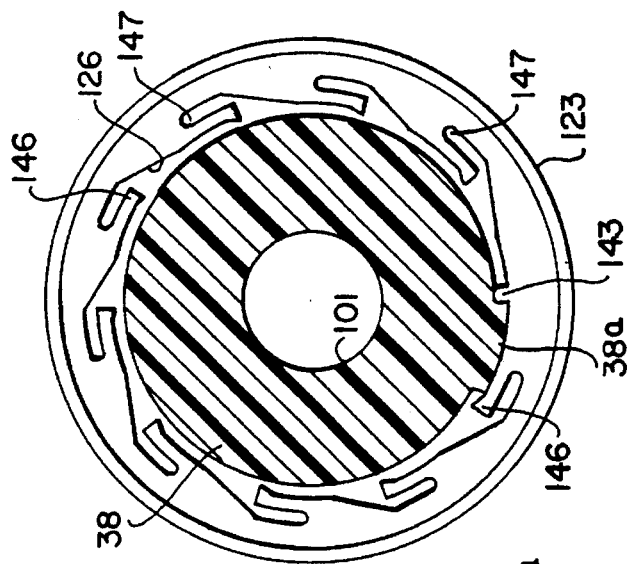
FIG. 13 is a cross-sectional view taken along the line 13—13 of FIG. 11.

In general, the medical device consists of a tool having a proximal extremity. The proximal extremity of the tool includes a collar which is affixed thereto and a cap. The cap includes a part which requires replacement and/or cleaning for each use of the tool. Cooperative means is carried by the cap and the collar and includes a rotatable number wheel and means for causing advancement of the number wheel and when the cap is separated from the collar so that the number wheel is advanced by one increment each time the cap is removed and/or replaced on the collar to give an indication of the number of times that the device has been used or the number of uses remaining.

More particularly, as shown in drawings, the medical device 11 consists of a replaceable and reusable tool 12 which is removably mounted in a tool actuating and holding mechanism or tool actuator 13 which is provided with the pistol grip 14 having a tubular extension 15 and having an actuating trigger 16 mounted therein. The actuator 13 can be of a type described in co-pending application, Ser. No. 07/806,666, filed Dec. 13, 1991, now U.S. Pat. No. 5,448,042 as explained therein the actuating and holding mechanism is adapted to have used therewith a plurality of removable tools of the type described in said co-pending application. A typical tool 12 is shown in FIG. 1 and as shown therein consists of a grasper 21 of the type described in co-pending application, Ser. No. 07/806,666, filed Dec. 13, 1991 now U.S. Pat. No. 5,448,042. The grasper 21 is carried by an elongated rigid tubular shaft 26 which is slidably mounted in a back up tube 27. A sleeve 28 is disposed over the back up tube 27 and over a collar or skirt 31. The collar 31 is secured to the proximal extremity of the shaft 26. The collar 31 is provided with a plurality of circumferentially spaced-apart windows 33 which are adapted to receive fingers 34 of a locking member 36 carried by the tubular member 26. The collar 31 is provided with a cylindrical extension 38 of reduced diameter which has an annular protrusion 39 formed thereon.

A removable cap 41 is provided which is adapted to be secured to the cylindrical extension 38 as hereinafter described. Typically the cap 41 carries a replaceable part which requires that it be replaced or cleaned specially after each use of the tool 12. Thus, as shown, a resilient valve 42 (see FIGS. 2 and 3) is removably mounted within the cap 41 in a cylindrical recess 43 and forms a seal with the annular protrusion 39 on the cylindrical extension 38. The cap 41 is provided with a centrally disposed bore 46 which is in alignment with the valve 42 and with the shaft 26.

Cooperative mating means is provided for removably securing the cap 41 to the cylindrical extension 38. The cooperative mating means includes a counter assembly 51 which includes a counter ring or wheel 52. The counter ring or wheel 52 is provided with a sloping surface having a plurality of circumferentially spaced-apart indicia in the form of arabic numerals 53 as hereinafter described to indicate the number of uses which are left rather than the number of uses which have occurred with respect to the tool. However, the counter wheel 52 can be used to count either up or down. Additional cooperative mating means are provided for snapping the counter ring 52 onto the cylindrical extension 38 and consists of an annular groove 54 in the counter ring 52 which snaps over an annular protrusion 57 on the cylindrical extension 38 to retain the counter ring 52 by preventing longitudinal movement while permitting rotational movement.

The cooperative mating means for securing the cap 41 to the cylindrical extension 38 comprises first and second L-shaped type recesses or slots 61 and 62 with bayonet-type entries which are formed 180° apart in the exterior surface of the cylindrical extension 38 as shown in FIGS. 6 and 7. As shown in those figures, each of the recesses or slots 61 and 62 is provided with inlet portions 61a and 62a which are substantially funnel-shaped. The portions 61a and 62a lead into portions 61b and 62b, respectively that extend directions parallel to the axis of the cylindrical extension 38. The portions 61b and 62b adjoin portions 61c and 62c, respectively and extend at right angles thereto or circumferentially of the cylindrical extensions 38. Another annular recess 63 is provided in the cylindrical extension 38 which is generally in registration with the bayonet type recess 61 that extends circumferentially in a direction at right angles to the axis of the cylindrical extension 38 and subtends an angle of approximately 90°.

The cooperative mating means also includes first and second buttons or protrusions 66 in the cap 41 (FIG. 8) which are spaced 180° apart and which are adapted to seat in and mate with the recesses 61 and 62 provided on the cylindrical extension 38. An L-shaped recess 67 is formed in the cap and extends inwardly from the distal extremity of the cap to provide a pawl 69 which has an inclined ramp 71 formed therein on the open side of the cap 41 which is inclined outwardly in a circumferential direction.

Three cooperating spaced-apart arcuate ramps 72, 73 and 74 are provided in one end of the counter ring or wheel 52 as shown in FIG. 4 which are inclined upwardly or outwardly in a clockwise direction as viewed in FIG. 4 followed by a spaced apart arcuate recess 76 which is of uniform depth. Arcuate portions 77, 78 and 79 of uniform height are disposed between the ramps 72, 73 and 74 and the recess 76. A longer arcuate portion 81 of the same height as portions 77, 78 and 79 is disposed between the end of the recess 76 and the commencement of the ramp 72. A stepdown 82 from the arcuate surface 81 occurs at the commencement of the ramp 72. This stepdown 82 represents the initial or starting point for counting as hereinafter described and has the pawl 69 positioned therein as shown in FIG. 4. Additional stepdowns 83, 84 and 85 are provided from the surfaces 77, 78 and 79 respectively into the arcuate ramps 73 and 74 and into the recess 76.

The other side or end of the counter ring or wheel 52 is provided with an annular recess 86 and with a centrally disposed hole or bore 87 which extends axially through the ring 52. A plurality of circumferentially spaced-apart arcuate ramps 88, 89, 91 and 92 are provided in the ring 52 and are spaced approximately 70° apart. Radial stepouts 93, 94, 95 and 96 are provided respectively for the commencement of the ramps 88, 89, 91 and 92 and extend outwardly from the cylindrical surface defining the bore 87.

A slot 97 is also formed in the counter ring 52 and opens into the hole 87 and is spaced approximately equidistant from the ramps 88 and 92. A semicircular counter pawl 98 (see FIG. 9) is provided and is formed of a suitable material, such as stainless steel. It can have a suitable thickness, as for example, 0.005 inches and a suitable width as for example, 0.070 inches. It is provided with an outwardly bent portion 98a at one end of an inwardly bent portion 98b at the other end. The portion 98a is adapted to seat in the slot 97 whereas the portion 98b is adapted to seat in a slot 99 provided at the base of the cylindrical extension 38. As shown in FIGS. 4 and 5, a hole 101 extends through the cylindrical extension 38.

The cap 41 when assembled as shown in FIGS. 2 and 3 of the drawings is adapted to have mounted thereon a suction and irrigation adapter 106 of a conventional type which has a cup-shaped member 107 frictionally retained on the cap 41 and has a cylindrical extension 108 therein which extends through the cap 41 and seats in the valve 42. The frictional retention is aided by an annular protrusion 109 provided on the exterior of the cap 41. The adapter 106 is provided with tubes 111 and 112 serve as an irrigation tube and a suction tube, respectively.

Operation and use of the medical device 11 with a counter therein for recording usage may now be briefly described as follows. Let it be assumed that a tool 12 has been assembled in the manner shown in the drawings and that it is desired to utilize the same in a hand held actuator, as for example the actuator 13 hereinbefore described to perform a laparoscopic procedure. After the laparoscopic procedure has been performed, the tool 12 can be removed from the actuator 13. Let it be assumed that it is now desired to utilize the tool 12 in connection with another laparoscopic procedure and that before doing so it is desired to clean and sterilize all parts of the tool. The cap 41 is removed by rotating it in a counter clockwise direction by the thumb and the index finger of the hand grasping the cap which has its cap pawl 69 in engagement with the leading edge of the ramp 72 and causes the counter ring or wheel 52 to rotate as the cap 41 is rotated. The next digit 53 appearing on counter ring 52 is now in registration with arrow 116 provided on the skirt 31. The amount of rotation is determined by the length of the slots 61c and 62c. While twisting the cap 41, the fingers of the hand can readily feel when the buttons 66 reach the ends of the slot portions 61c and 62c. The cap 41 then can be pulled proximally to cause the buttons or protrusions 66 to travel in the slot portions 61b and 62b to permit the cap to be separated from the cylindrical extension 38. The cap 41 with the valve 42 therein can be discarded. A flushing cap (not shown) to which a syringe can be attached is placed over the cylindrical extension 38 to flush out the interior of the tool 12. The flushing cap can then be removed with no effect on the counter wheel 52. Thus, the flushing cap can be put in place and removed without affecting the counter wheel.

A new cap 41 with a new valve 42 therein is placed over and into the cylindrical extension 38 by registering the protrusions or buttons 66 with the bayonet type entrance slot portion 61a and 62a and then pushing the cap 41 inwardly over the cylindrical extension 38 so that they bottom out in the slot portions 61b and 62b. The cap 41 is then rotated in a clockwise direction so that the buttons 66 travel in the slot portions 61c and 62c. Rotation of the cap 41 can continue until the cap pawl drops off over the stepdown 83 into the deepest part of the inclined ramp 73. Further rotation of the cap 41 cannot occur because the buttons 66 are seated at the extremities of the slot portions 61c and 62c. The counter wheel 52 is prevented from being rotated in a clockwise direction by the use of the substantially semicircular counter pawl 98 which it has its end portion 98a seated against one of the stepouts 93–96.

The tool 12 is now ready to be sterilized with its new cap 41 and the valve 42 therein. Typically, this sterilization can take place in a conventional autoclave where it is subjected to a temperature of approximately 275 degrees Fahrenheit.

After cleaning and sterilization, the tool 12 is ready for use and can be placed into the actuator 13 and let it be assumed that it has in fact been used. After use, the cap 41 is removed by rotating it in a counterclockwise direction. As this counterclockwise rotation occurs, cap pawl 69 engages the stepdown 83 of the ramp 73 and causes counterclockwise rotation of the counter wheel. Typically such movement can subtend a certain angle as for example an angle of 76 degrees. The limit of the counter clockwise rotation is limited by the other extremity of the slot portions 61c and 62c.

As the counter wheel 52 is rotated in a counterclockwise direction, the ramp 89 engages the out turned portion 98a and depresses that portion of the counter pawl 98 into the recess 63 in the cylindrical extension 38. This continues until the portion 98a is released at the stepout 95 permitting it to spring back into the deepest part of the ramp surface 91. This juxtaposition of portion 98a of counter pawl 98 and stepout 95 serves to prevent clockwise motion of the counter wheel 52. At this point, the buttons or protrusion 66 are at the end of the slot portions 61c and 62c permitting the cap 41 with the valve 42 to be removed and discarded. After cleaning and flushing of the tool 12 as hereinbefore described, a new cap 41 and a new valve 42, if applicable, can then be positioned on the cylindrical extension 38 by causing the protrusions or buttons 66 to enter into the L-shaped slots 61 and 62. Thereafter, the cap 41 is locked in position by rotating it in a clockwise direction. Because of the counter pawl 98 and shape of the ramps 72–74, and 76, rotation of the cap 41 in a clockwise direction cannot cause similar clockwise motion of the counter wheel 52. The counter wheel 52 is locked in a predetermined clockwise position by the portion 98a engaging the stepout 95 at deepest portion of the ramp 91. Thereafter, the tool can be sterilized hereinbefore described.

If it is desired to reutilize the tool 12 in another procedure, the cap 41 and the valve 42 therein can be removed by rotation in a counterclockwise direction to advance the counter wheel 52 another digit after which the cap 41 and the valve 42 therein can be discarded and a new cap with a new valve, if applicable, inserted therein and be placed on the 38 extension and the same procedure repeated. This procedure can be repeated until the last digit has been reached on the counter wheel which means that the tool has been used to the extent of usage permitted within the warranty. After that point in time if the user still continues to use the tool, the user is using it out of warranty and at the user's risk. At the time, that the last position is reached, the pawl portion 98a drops into the recess 97 and remains there because there are no more ramps which are available on the counter wheel 52 to push the counter wheel pawl 98 into the recess 63. This prevents rezeroing of the counter wheel 52.

Figure 11:
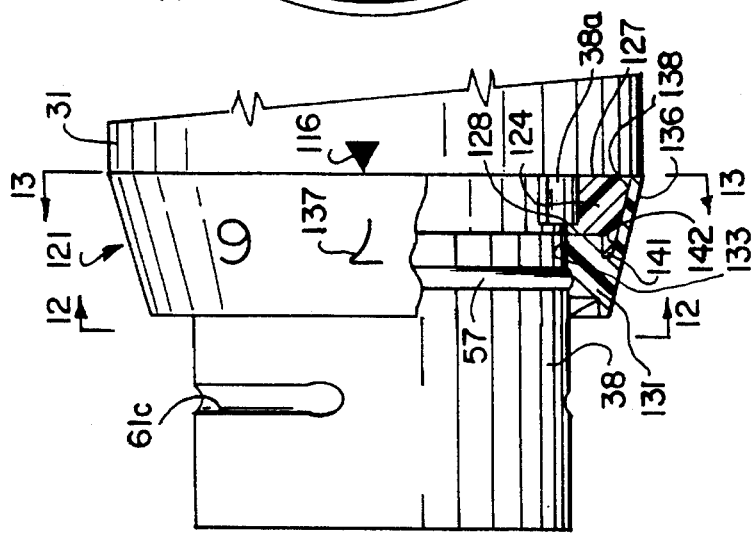
FIG. 11 is a partial side elevational view of a tool similar to that shown in FIGS. 1 and 2 partially in cross section showing another embodiment of a counter incorporating the present invention.
Figure 12:
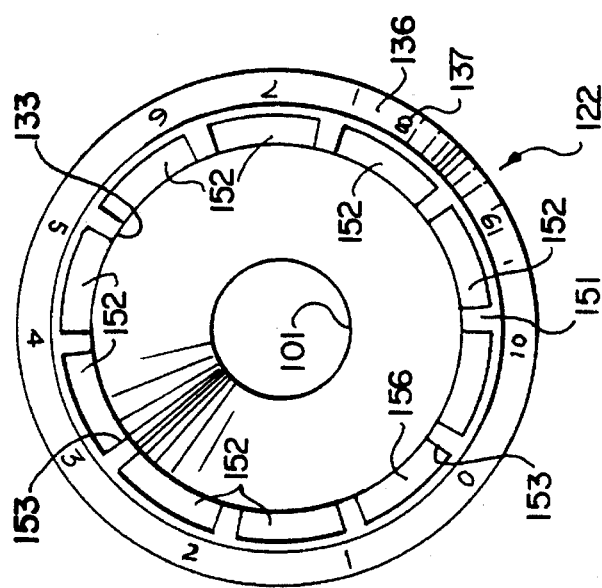
FIG. 12 is a cross-sectional view taken along the line 12—12 of FIG. 11.

Another embodiment of a counter for recording usage of a tool is shown in FIGS. 11, 12 and 13. As shown therein, the skirt 31 with a cylindrical extension 38 are substantially identical to the skirt 31 and the cylindrical extension 38 hereinbefore described in connection with the previous embodiments with the exception that an arcuate protrusion 38a (see FIG. 13) has been provided on the outer surface of the cylindrical extension 38. A cap 41 identical to that hereinbefore described is utilized with the cylindrical extension and is provided with cooperative mating means of the type hereinbefore described for the cap 41 and the cylindrical extension 38.

In order to simplify construction of the counter assembly and to make it possible to eliminate the counter pawl 98, a modified counter assembly 121 has been provided which includes a counter wheel 122 and a counter indexer 123. The counter indexer 123 fits within the counter wheel 122 and both fit over the cylindrical extension 38. The counter wheel 122 and the counter indexer 123 can be formed of a suitable plastic material such as ULTEM 1000 which is a plastic suitable for medical uses. The counter indexer 123 is provided with an annular body 124 which has a large opening 126 therein to accommodate the cylindrical extension 38. It is also provided with a planar wall 127 which travels on the skirt 31. It is also provided with another wall 128 parallel to the wall 127.

The counter wheel 122 is provided with an annular body 131 which has a wall 132. The body 131 is provided with a bore 133 which corresponds to the size of the cylindrical extension 38 so that the counter wheel 122 can rotate thereon. The body 131 is provided with a sloping exterior surface 136 which carries therein indicia 137 going from 0–10 as shown in approximate positions in FIG. 12. The body 131 is provided with an annular recess 138 which is shaped to receive the body 124 of the counter indexer 123 with a relatively close fit. Cooperative means is carried by the counter wheel 122 and the counter indexer 123 to assure that they are registered properly with respect to each other when they are assembled and fastened together with suitable means such as by an adhesive or solvent (not shown). This cooperative registration means consists of an upstanding lug 141 which is provided on the counter indexer 123 which is disposed in a recess 142 in the counter wheel to provide a precise rotational relationship between the counter indexer 123 and the counter wheel 122. If desired, the counter indexer 123 and the counter wheel 122 may be formed in one piece. An inwardly extending protrusion 143 is provided on the counter indexer 123 which is used for a purpose hereinafter described.

A plurality of circumferentially spaced arms 146 are provided as a part of the counter indexer 123 and are formed integrally therewith. Slots 147 are provided behind the arms to permit the arms to be deflected inwardly into the slots 147 as hereinafter described. As shown in FIG. 13, these arms 146 are adapted to be engaged by the protrusion 38a carried by the cylindrical extension 38. Thus, it can be seen that the arms 146 are cammed outwardly in a radial direction by the protrusion 38a engaging the arms as the counter wheel 122 and the counter indexer 123 are rotated in a counterclockwise direction. When the protrusion 38a clears each of the arms 146 the arms 146 snap back into their normal position and serve as stops to prevent rotation of the counter wheel 122 and the associated counter indexer 123 in a clockwise direction.

The other side of the body 131 is provided with a wall 151 in which there are provided a plurality of ramps 152, as for example, ten if it is desired to have nine counts on the counter assembly 121. These ramps 152 are formed by step downs 153 from the wall 151 with the ramps 152, when viewed in the clockwise direction shown in FIG. 2, being inclined upwardly and outwardly until they reach the surface or wall 151. An arcuate recess or trough 156 is provided between the nine ramps 152.

Operation and use of the tool with the counter assembly 121 hereinbefore described is very similar to that hereinbefore described for use with the counter assembly 51. A cap 41 with a valve 42, if applicable, would be inserted over and into the cylindrical extension 38 with the buttons 66 in engagement with the L-shaped recesses 61 and 62 provided in the cylindrical extension 38. Each time that the cap 41 is removed after use of the tool, the cap 41 is rotated in a counterclockwise direction with the cap pawl 69 engaging a stepdown 153 into the recess 152 and causing rotation of the counter wheel 122 and the counter indexer 123. Travel is arrested when the buttons 66 reach the portions 61b and 62b of the L-shaped slots 61 and 62. The counter assembly 121 cannot be rotated in a clockwise direction because the extremities of the arms 146 engage the protrusion 38a to prevent such rotation.

The cap 41 can then be slipped off with the buttons traveling through the slot portions 61b and 62b. After cleaning, a new cap 41 with a new valve 42, if applicable, therein can then be placed on the tool and the tool sterilized in the manner hereinbefore described. After the tool has been sterilized and reused, the cap can be removed in the manner hereinbefore described by having the cap pawl 69 engage the next step down 153 to again advance the counter wheel 122 and the counter indexer 123 by another increment. The cap 41 can then be removed and replaced as hereinbefore described. This procedure can continue until the tenth time at which the time the protrusion 38a on the cylindrical extension 38 ends up between the inwardly extending protrusion 143 provided on the counter indexer 123 and the distal extremity of the nearest arm 146. This prevents rezeroing of the counter wheel 122. The tool, however, can still be used by removing the cap and inserting a new cap. The count, however, will remain the same to indicate that nine uses have occurred and that the warranty has expired. The counter wheel 122 can not rotate because it is locked between protrusion 143 and the last pawl of the indexer 123. The last ramp is in fact not a ramp but of equal depth throughout. Thus, it will not deflect the cap pawl and allow it to drop into the next ramp but only allows the cap pawl limited travel within it which has no effect on advancing the counter wheel 122.

It is apparent from the foregoing that there has been provided a counter for recording usage on medical tools and devices. The outline of the counter fits within the confines of the tool and is very compact. Its construction is relatively simple and is comprised of few parts so that it can be economically manufactured.

What is claimed is:

1. A surgical device having a counter for recording usage, comprising a tool and a tool actuator having the tool removably mounted thereon and including means for actuating the tool, said tool having a proximal extremity, said tool comprising a collar and a cap removable mounted on the collar, said cap including a part which requires replacement and/or cleaning for each use of the tool, cooperative mating means carried by the cap and the collar and including a rotatable counter wheel having a plurality of circumferentially spaced apart numbers thereon and also including means for causing advancement of the counter wheel from one number to the next number when the cap is separated from the collar so that the counter wheel is advanced by one increment each time the cap is removed from the collar to give an indication of the number of times that the device has been used.

2. A device as in claim 1 wherein said cooperative mating means includes means engaging said counter wheel and permitting rotation of said counter wheel in one direction and preventing rotation of said collar in an opposite direction.

3. A device as in claim 1 wherein said collar is provided with a cylindrical extension and wherein said counter wheel is rotatably mounted on the extension of said collar, said cooperative means including at least one L-shaped slot and a protrusion for traveling in said L-shaped slot, the cooperative means carried by the collar being disposed on the cylindrical extension.

4. A medical device as in claim 1 wherein said counter wheel is provided with a plurality of circumferentially spaced-apart ramps and stepdowns entering into the ramps and wherein said cap is provided with a cap pawl adapted to travel on said ramps and engage said stepdowns.

5. A device as in claim 4 wherein said cooperative mating means for permitting rotation of the counter wheel in one direction and preventing rotation of the counter wheel in the opposite direction includes a yieldable member adapted to be moved out of engagement during incremental rotation of the counter wheel and preventing rotation of the counter wheel in the opposite direction.

6. A surgical device having a counter for recording usage comprising a tool having a proximal extremity, said tool having a collar affixed thereto and a cap, said cap having a centrally disposed flow passage therein through which a fluid can be introduced and a valve for closing off said flow passage, cooperative mating means carried by the cap and the collar including a counting mechanism for displaying a plurality of sequential numbers connoting usage of the device, said counting mechanism including a movable member advanceable by increments to display each of said sequential numbers one-by-one in sequence, said counting mechnism also including means for causing advancement of the movable member to display the next sequential member when the cap is separated from the collar so that the movable member is advanced by one increment each time the cap is removed from the collar to give an up-to-date indication of the number of times the device has been used.

* * * * *

UNITED STATES PATENT AND TRADEMARK OFFICE
CERTIFICATE OF CORRECTION

PATENT NO. : 5,519,197
DATED : May 21, 1996
INVENTOR(S) : Robinson, et al.

It is certified that error appears in the above-indentified patent and that said Letters Patent is hereby corrected as shown below:

On title page, item [54] and col. 1, should read as follows:

"SURGICAL DEVICE WITH COUNTER FOR RECORDING USAGE"

Signed and Sealed this

Twenty-third Day of July, 1996

Attest:

BRUCE LEHMAN

Attesting Officer    Commissioner of Patents and Trademarks